(12) United States Patent
Timofeyev et al.

(10) Patent No.: US 10,898,093 B2
(45) Date of Patent: Jan. 26, 2021

(54) SCAR ASSESSMENT

(71) Applicant: BIOSENSE WEBSTER (ISRAEL) LTD., Yokneam (IL)

(72) Inventors: Michael Timofeyev, Nesher (IL); Tal Haim Bar-on, Kiryat Tivon (IL); Gal Hayam, Tivon (IL); Inbal Dubiner, Kazir (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 176 days.

(21) Appl. No.: 16/231,995

(22) Filed: Dec. 25, 2018

(65) Prior Publication Data

US 2020/0196891 A1 Jun. 25, 2020
US 2020/0315483 A9 Oct. 8, 2020

Related U.S. Application Data

(60) Provisional application No. 62/623,022, filed on Jan. 29, 2018.

(51) Int. Cl.
*A61B 5/04* (2006.01)
*A61B 5/042* (2006.01)
*A61B 5/0456* (2006.01)

(52) U.S. Cl.
CPC ........ *A61B 5/04011* (2013.01); *A61B 5/0422* (2013.01); *A61B 5/0456* (2013.01)

(58) Field of Classification Search
CPC .. A61B 5/04011; A61B 5/0456; A61B 5/0422
USPC ........................................ 600/508
See application file for complete search history.

(56) References Cited

U.S. PATENT DOCUMENTS

| 2002/0045810 | A1 | 4/2002 | Ben-Haim |
| 2009/0099468 | A1 | 4/2009 | Thiagalingam et al. |
| 2011/0230775 | A1* | 9/2011 | Barley ...................... A61B 6/12 |
| | | | 600/508 |
| 2016/0331262 | A1 | 11/2016 | Kuck et al. |
| 2017/0011197 | A1* | 1/2017 | van Dam ............... G16H 50/50 |

OTHER PUBLICATIONS

European Search Report dated Jun. 14, 2019 from corresponding European Patent Application No. 19154002.0.
(Continued)

*Primary Examiner* — Amanda K Hulbert
*Assistant Examiner* — Philip C Edwards

(57) ABSTRACT

Apparatus for assessing scarring of cardiac tissue, consisting of a probe and a processor. The probe has one or more electrodes, which are configured to contact the tissue at a plurality of positions and to sense respective voltages in the tissue at the positions. The processor receives the respective voltages, and computes a triangular mesh that is representative of a surface of the tissue and that consists of multiple triangles having vertices corresponding to the positions contacted by the one or more electrodes. The processor calculates respective scar areas within the triangles by comparing the respective voltages sensed at the positions corresponding to the vertices to a predefined range of the voltages that is associated with scarring, and computes a sum of the respective areas. The processor compares the sum to a total area of the triangles so as to assess a degree of the scarring of the tissue.

14 Claims, 7 Drawing Sheets

(56) References Cited

OTHER PUBLICATIONS

Kuklik, P. et al: "The reconstruction, from a set of points, and analysis of the interior surface of the heart chamber; Reconstruction and analysis of the interior surface of the heart", Physiological Measurement, Institute of Physics Publishing, Bristol, GB, vol. 25, No. 3, Jun. 1, 2004, pp. 617-627.

Eran, Leshem et al., "High-Resolution Mapping of Ventricular Scar", JACC: Clinical Electrophysiology, vol. 3, No. 3, Mar. 1, 2017, pp. 220-231.

* cited by examiner

| TRIANGLE | TRIANGLE VERTEX VERTEX VOLTAGE | | | VOLTAGE MINIMUM | VOLTAGE MAXIMUM | POLYGON AREA |
| | A $a_1$ | B $a_2$ | C $a_3$ | $a_{min}$ | $a_{max}$ | TRIANGLE AREA |
|---|---|---|---|---|---|---|
| 1 | (0,0) 1 | (2,3) 2 | (4,0) 1 | 1 | 2 | 6 / 6 |
| 2 | (0,0) 2 | (2,3) 4 | (4,0) 3 | 1 | 2 | 0 / 6 |
| 3 | (0,0) 0 | (2,3) 2 | (4,0) 2 | 1 | 2 | 4.5 / 6 |
| 4 | (0,0) 4 | (2,3) 0 | (4,0) 4 | 1 | 2 | 1.875 / 6 |
| 5 | (0,0) 0 | (2,3) 2 | (4,0) 4 | 1 | 2 | 2.25 / 6 |
| 6 | (0,0) 1 | (2,3) 6 | (2,0) 3 | 3 | 5 | 1.6 / 3 |
| 7 | (0,0) 0 | (2,3) 2 | (4,0) 4 | 1 | 3 | 4.5 / 6 |

FIG. 5

SCAR ASSESSMENT

CROSS-REFERENCE TO RELATED APPLICATION

This application claims the benefit of U.S. Provisional Patent Application 62/623,022, filed 29 Jan. 2018, which is incorporated herein by reference.

FIELD OF THE INVENTION

This invention relates generally to investigating human tissue, and specifically to assessing a degree of scarring of cardiac tissue.

BACKGROUND OF THE INVENTION

In diagnosing problems associated with the heart, it is well known that scarring of portions of the myocardium may contribute to the problems, and this is considered to be the case, for example, in atrial fibrillation. The scarring can be identified non-invasively using magnetic resonance imaging (MRI) protocols, and/or invasively using bipolar voltage mapping.

SUMMARY OF THE INVENTION

An embodiment of the present invention provides apparatus for assessing scarring of cardiac tissue, consisting of:
a probe including:
one or more electrodes, which are configured to contact the cardiac tissue at a plurality of positions and to sense respective voltages in the tissue at the positions; and
a processor which is configured to:
receive the respective voltages,
compute a triangular mesh that is representative of a surface of the cardiac tissue and that has multiple triangles having vertices corresponding to the positions contacted by the one or more electrodes,
calculate respective scar areas within the triangles by comparing the respective voltages sensed at the positions corresponding to the vertices to a predefined range of the voltages that is associated with scarring, and
compute a sum of the respective areas, and compare the sum to a total area of the triangles so as to assess a degree of the scarring of the tissue.

Typically the voltages are peak-peak bipolar voltages.

In a disclosed embodiment the range includes a minimum voltage associated with the scarring of the tissue and a maximum voltage associated with the scarring of the tissue. Typically, the disclosed embodiment includes, for a given triangle in the multiple triangles, associating the minimum and maximum voltages with edges of the given triangle so as to define points on the edges. The disclosed embodiment may also include joining the points to form a polygon, wherein the polygon includes, for the given triangle, the respective scar area.

In a further disclosed embodiment the one or more electrodes consist of two electrodes.

In a yet further disclosed embodiment the probe further includes a sensor configured to provide respective signals to the processor indicative of the positions.

In an alternative embodiment the one or more electrodes are configured to provide respective signals to the processor indicative of the positions.

In a further alternative embodiment the predefined range is selected for the scarring of the tissue to consist of dense scar. Alternatively or additionally, the predefined range is selected for the scarring of the tissue to consist of hibernating myocardium.

There is further provided, according to an embodiment of the present invention, a method for assessing scarring of cardiac tissue, including:
contacting the cardiac tissue with one or more electrodes at a plurality of positions;
sensing respective voltages in the tissue at the positions;
computing a triangular mesh that is representative of a surface of the cardiac tissue and that consists of multiple triangles having vertices corresponding to the positions contacted by the one or more electrodes;
calculating respective scar areas within the triangles by comparing the respective voltages sensed at the positions corresponding to the vertices to a predefined range of the voltages that is associated with scarring; and
computing a sum of the respective areas, and comparing the sum to a total area of the triangles so as to assess a degree of the scarring of the tissue.

The present disclosure will be more fully understood from the following detailed description of the embodiments thereof, taken together with the drawings, in which:

BRIEF DESCRIPTION OF THE DRAWINGS

FIG. 5 is a table illustrating numerical examples of different triangles, polygons generated for the triangles, and the area of each of the polygons, according to an embodiment of the present invention;

DETAILED DESCRIPTION OF EMBODIMENTS

Overview

Figure 1:
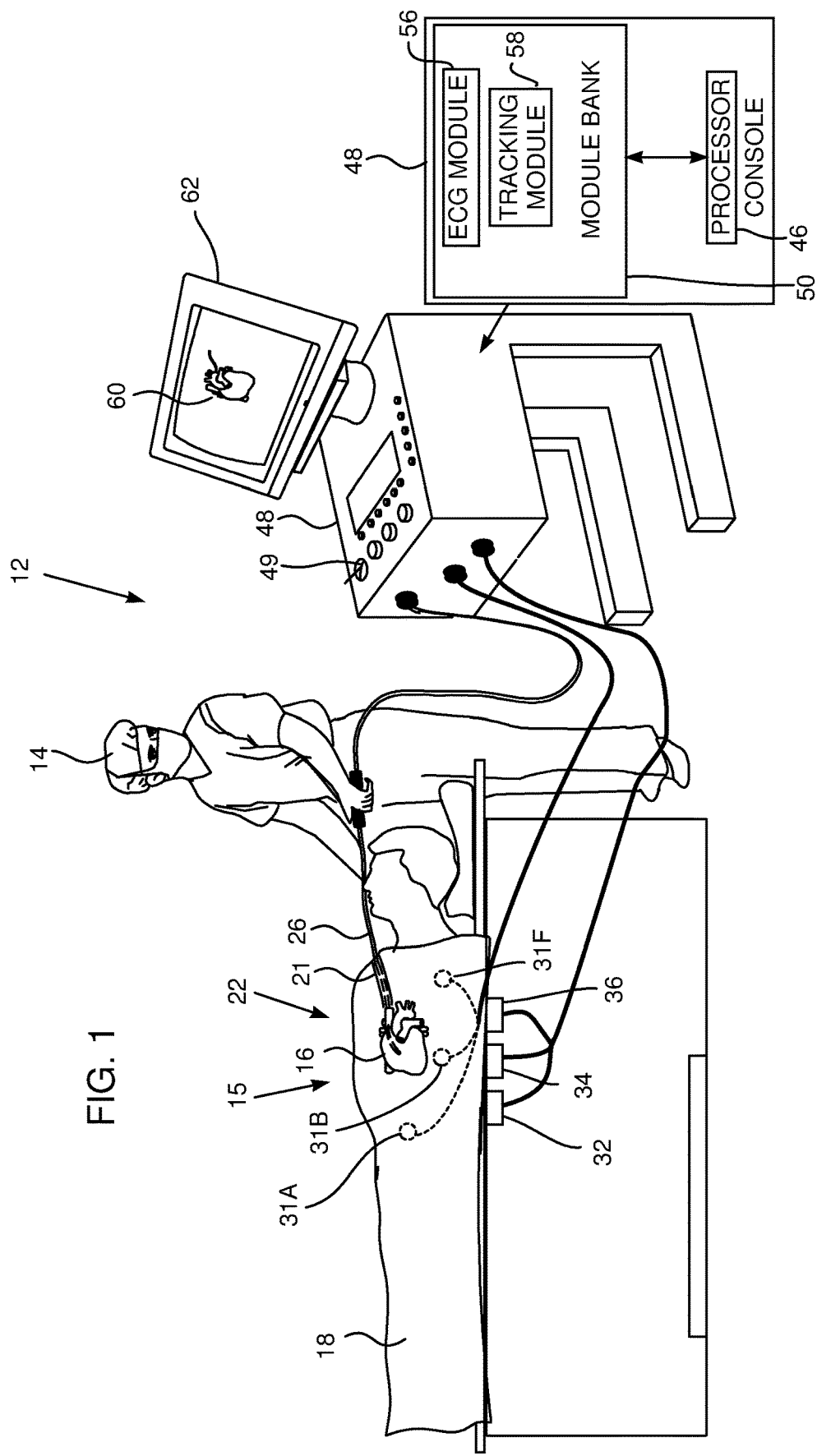
FIG. 1 is a schematic illustration of an invasive medical procedure using an apparatus, according to an embodiment of the present invention.

In analyzing cardiac tissue, the assessment of the degree of scarring of the tissue, also termed the scar burden, has been fraught with difficulty. For example, if a non-invasive MRI (magnetic resonance imaging) protocol is used the complexity and limited availability of the MRI protocol causes problems. For an invasive assessment using bipolar voltages, the lack of consistency of the bipolar sampling techniques and measurement is also problematic. In many cases the assessment of scar burden relies on a visual estimation, and this has been shown to be inaccurate.

Embodiments of the present invention provide a quantitative and objective assessment of the scar burden associated with cardiac tissue being investigated. In a procedure performed on a patient, a probe is introduced into the patient, and the probe is used to acquire positions in the tissue and corresponding bipolar voltages associated with the positions. From the positions a triangular mesh is generated, and a respective bipolar voltage is associated with each vertex of every triangle in the mesh. Minimum and maximum bipolar voltages, that may be used in identifying scarred tissue, are applied to edges of the triangles, so as to define points on the edges. For a given triangle the points are connected, together with at least one or more sections of the edges of the triangle, to form a polygon within the triangle, so that the region within the polygon corresponds to an area of scarred tissue.

A quantitative assessment of the scar burden may be made by finding a ratio of the areas of all the polygons to the areas of all the triangles of the mesh.

A disclosed embodiment of the present invention provides apparatus for assessing scarring of cardiac tissue, the apparatus comprising a probe and a processor coupled to the probe.

The probe has one or more electrodes, typically a pair of electrodes, which are configured to contact the cardiac tissue at a plurality of positions and to sense respective voltages, typically bipolar voltages, in the tissue at the positions.

The processor receives the voltages from the probe. The processor also computes a triangular mesh that is representative of a surface of the cardiac tissue and comprises multiple triangles having vertices corresponding to the positions contacted by the one or more electrodes.

The processor calculates respective scar areas within the triangles by comparing the respective voltages sensed at the positions corresponding to the vertices to a predefined range of the voltages that is associated with scarring. A sum of the respective areas is computed, and the sum is compared to a total area of the triangles so as to assess a degree of the scarring of the tissue.

DETAILED DESCRIPTION

In the following description, like elements in the drawings are identified by like numerals, and like elements are differentiated as necessary by appending a letter to the identifying numeral.

Figure 2:
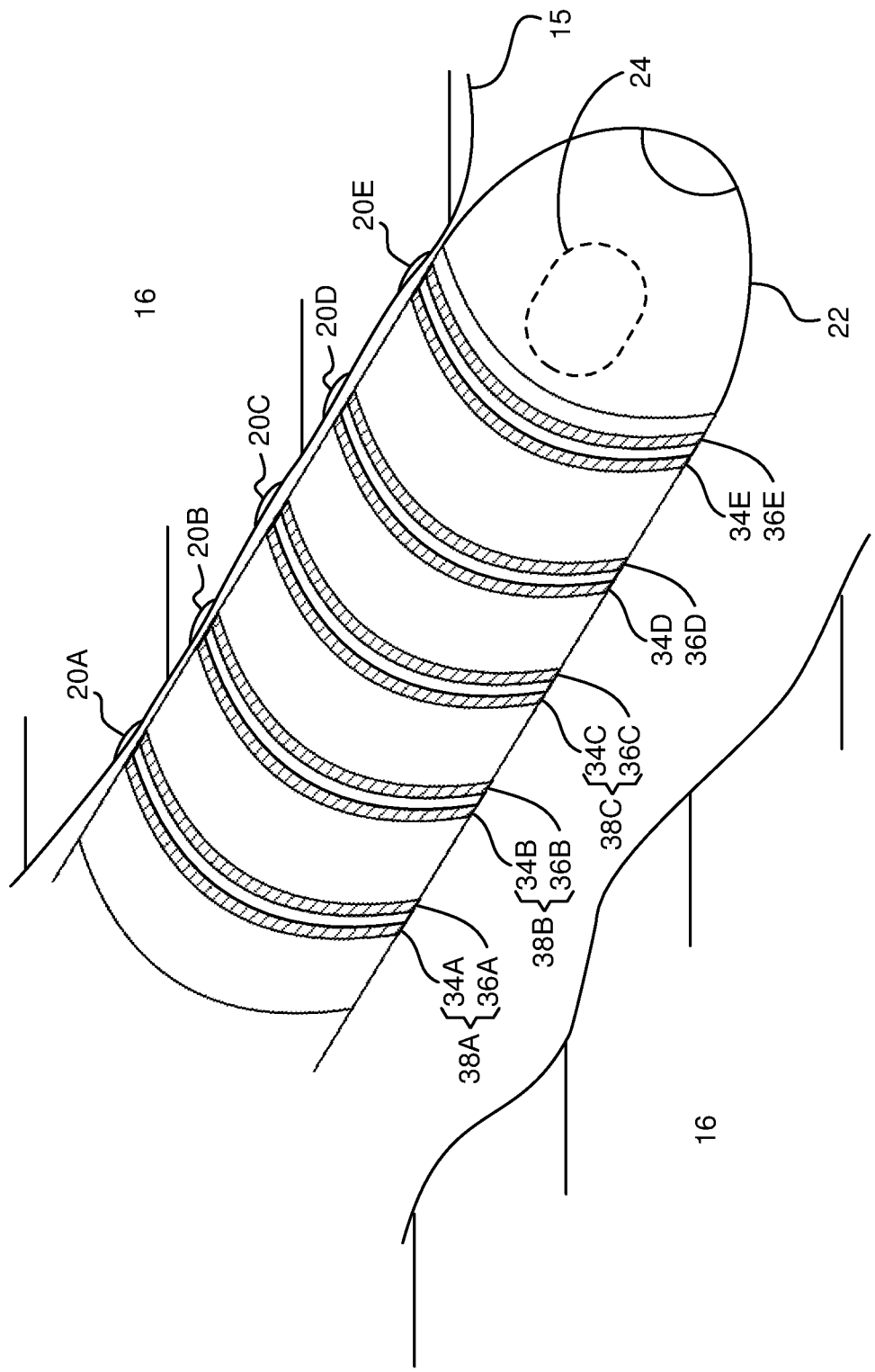
FIG. 2 is a schematic illustration of a distal end of a probe used in the apparatus, according to an embodiment of the present invention.

FIG. 1 is a schematic illustration of an invasive medical procedure using apparatus 12, and FIG. 2 is a schematic illustration of a distal end 22 of a probe 26 used in the apparatus, according to an embodiment of the present invention. The procedure is performed by a medical professional 14, and, in the description hereinbelow the procedure is assumed to comprise an investigation comprising electropotential mapping of at least a portion of tissue 15 of a myocardium 16 of the heart of a human patient 18.

The investigation also comprises using the mapping to analyze tissue 15 to find out how scarred the tissue is. The investigation may use results that have been previously acquired, i.e., as a retrospective investigation. Alternatively or additionally, the investigation may use results acquired in real time, i.e., as a real time investigation.

In order to perform the investigation, professional 14 inserts probe 20 into a sheath 21 that has been pre-positioned in a lumen of the patient. Sheath 21 is positioned so that distal end 22 of the probe enters the heart of the patient. Distal end 22 comprises a position sensor 24 that enables the location and orientation of the distal end to be tracked.

As is illustrated in FIG. 2, distal end 22 comprises generally similar pairs of cylindrical electrodes 34, 36, e.g. electrodes 34A, 36A; 34B, 36B; 34C, 36C; . . . . In the disclosure, for simplicity a pair of electrodes 34, 36 may also be referred to as electrodes 38, so that, for example, electrodes 34A, 36A may also be referred to as electrodes 38A. Electrodes 38 acquire electropotentials of regions with which they are in contact, and in the following description electrodes 38A, 38B, 38C, . . . are assumed to be respectively in contact with locations 20A, 20B, 20C, . . . of the myocardium.

Apparatus 12 is controlled by a system processor 46, which is located in an operating console 48 of the apparatus. Console 48 comprises controls 49 which are used by professional 14 to communicate with the processor. The software for processor 46, which comprises software for an algorithm described hereinbelow, may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 that is displayed on a screen 62.

In order to operate apparatus 12, processor 46 communicates with a module bank 50, which has a number of modules used by the processor to operate the apparatus. Thus, bank 50 comprises an electrocardiograph (ECG) module 56 which acquires and analyzes signals from electrodes 38, and a tracking module 58 which receives and analyzes signals from position sensor 24, and which uses the signal analysis together with the processor to generate a location and an orientation of distal end 22, as well as a location and orientation of electrodes 38. In some embodiments sensor 24 comprises one or more coils which provide the sensor signals in response to alternating magnetic fields traversing the coils. In these embodiments, in addition to receiving and analyzing signals from sensor 24, tracking module 58 also controls radiators 32, 34, and 36 which radiate the alternating magnetic fields traversing sensor 24. The radiators are positioned in proximity to myocardium 16, and are configured to radiate the alternating magnetic fields into a region in proximity to the myocardium. The Carto® system produced by Biosense Webster, of 33 Technology Drive, Irvine, Calif. 92618 USA, uses such a magnetic tracking system.

ECG module 56 typically acquires, from electrodes 38, bipolar voltages of the region in contact with the electrodes. In some embodiments one or both electrodes 34, 36 (of a given set of electrodes 38) may be used to acquire unipolar voltages from regions in contact with the electrodes. In some embodiments one or both electrodes 34, 36 may also be configured to apply ablation. Additionally or alternatively, one or both electrodes 34, 36 may be used as location sensing electrodes, determining a location in contact with the electrodes. The use as location sensing electrodes is described in more detail below.

Alternatively or additionally, embodiments of the present invention may incorporate other modes of tracking distal end 22 and electrodes 38. As one example, tracking module 58 may be configured to inject current into a given one of electrodes 38, and the module may record values of currents received by skin patches 31A, 31B, . . . 31F. There are typically six such patches, three of which are shown in the figure, attached to patient 18. The position of the given electrode may be estimated from the values of the currents acquired by the patches, and/or by the impedances of the patches, as registered by the module.

As a second example, tracking module 58 may be used to generate, again using skin patches attached to the patient, electric fields (typically three approximately orthogonal fields) in the patient, and the module may record the voltages generated on a given one of electrodes 38 in response to the fields. The position of the given electrode may be estimated from the recorded voltages. All such modes of tracking are assumed to be comprised within the scope of the present invention.

Bank 50 typically also comprises other modules, such as a force module, a power module, an irrigation module, and a temperature module. For simplicity the functions of these modules are not described herein.

For the electropotential mapping investigation described herein, distal end 22 is moved so that electrodes 38 contact different regions of tissue 15. While the electrodes are in contact, processor 46 uses ECG module 58 to acquire and record cardiac electropotentials generated during the period of contact. Also while the electrodes are in contact, the processor uses tracking module 58 to determine and record the position of the contacting electrodes. It will be understood that the position of the contacting electrodes is a three-dimensional position.

In an embodiment of the present invention, the cardiac electropotentials acquired by electrodes 38 and recorded by module 56 are bipolar voltages. Processor 46 analyzes the recorded bipolar voltages from a given set of electrodes 38 to find a peak-peak voltage value for the set of electrodes. Typically, the processor interpolates the peak-peak voltage values from locations in proximity to a given recorded position to find a peak-peak voltage for the given position. Thus for each recorded position on tissue 15, processor 46 is able to generate an ordered pair of values comprising a value of the position, and a peak-peak voltage value of electropotentials recorded by the electrodes for the recorded position.

Figure 3:
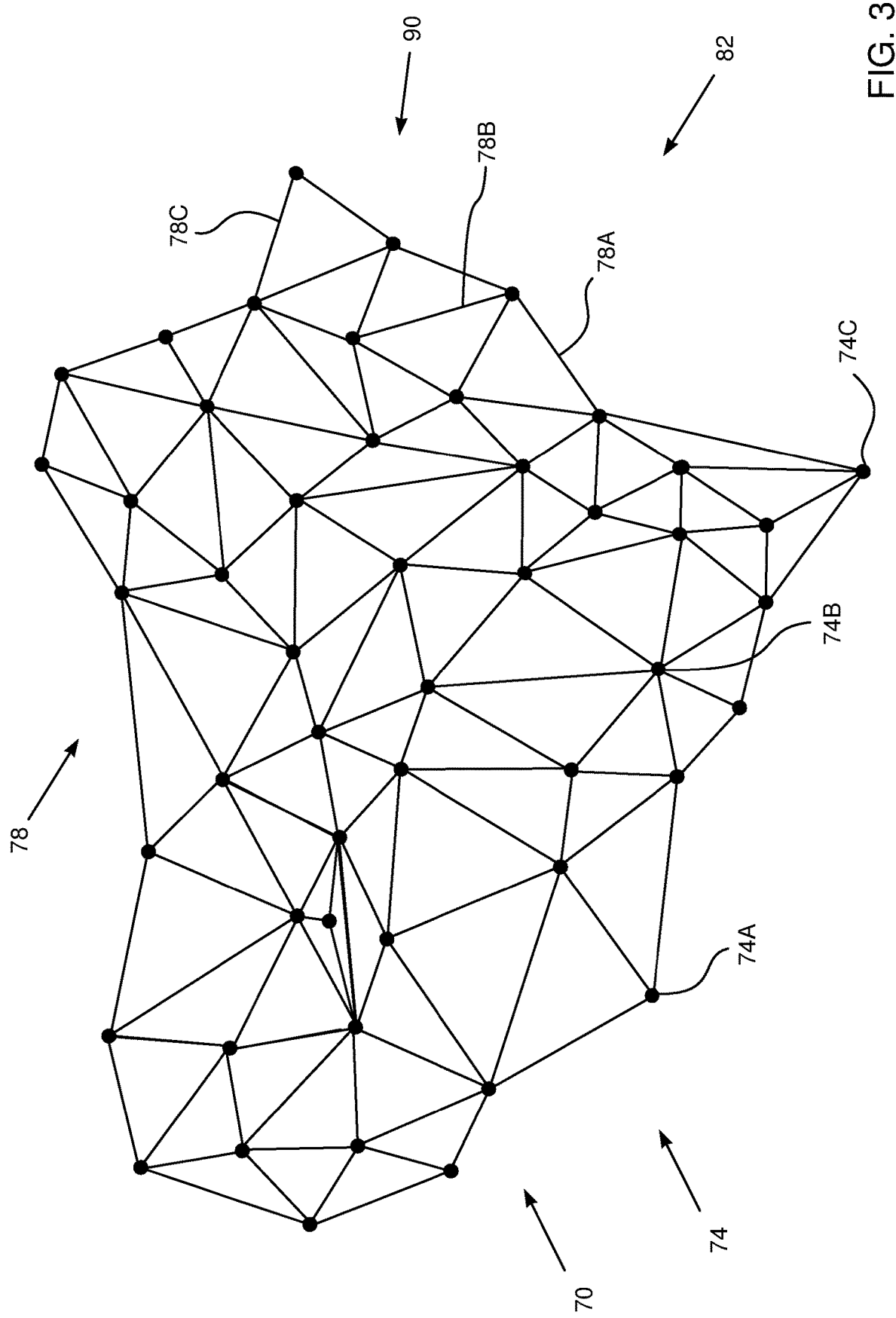
FIG. 3 schematically illustrates an array of recorded positions and line segments joining the positions to form a mesh, according to an embodiment of the present invention.

FIG. 3 schematically illustrates an array of recorded positions and line segments joining the positions to form a mesh, according to an embodiment of the present invention. As stated above, electrodes 38 and/or sensor 24 are used by processor 46 to acquire and record positions of the electrodes, herein referred to as recorded positions 74A, 74B, 74C, . . . , and generically as recorded positions 74. Recorded positions 74 form an array 70 of positions. Using processes well-known in the art processor 46 joins array 70 of recorded positions 74 by line segments 78A, 78B, 78C, . . . , generically referred to herein as line segments 78, for example by using a ball-pivot algorithm. In embodiments of the present invention, line segments 78 are generated so as to join positions 74 in a triangular mesh 82 comprising multiple triangles 90. While mesh 82 is typically in three dimensions, it will be understood that each triangle 90 of the mesh is a planar, two-dimensional (2D), triangle.

Each position 74 is at the vertex of at least one triangle, and is typically at the vertex of many triangles. There is a respective peak-peak voltage associated with each vertex.

Figure 4A:
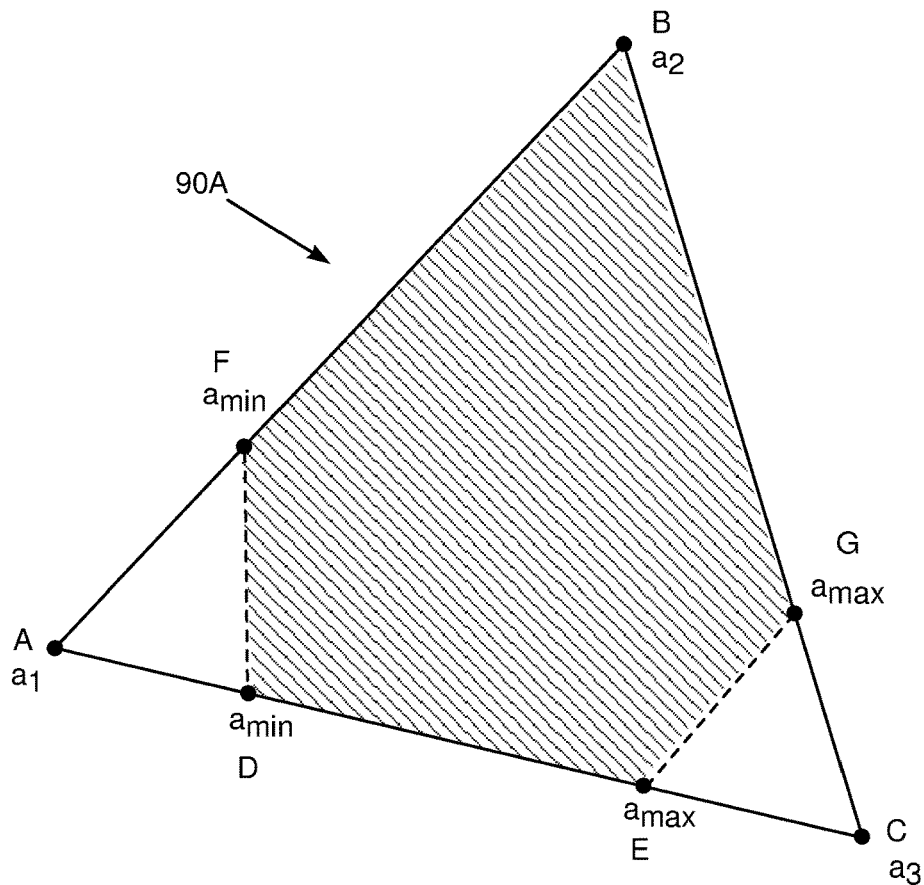
FIG. 4A is a schematic diagram illustrating a typical triangle of the mesh.
Figure 4B:
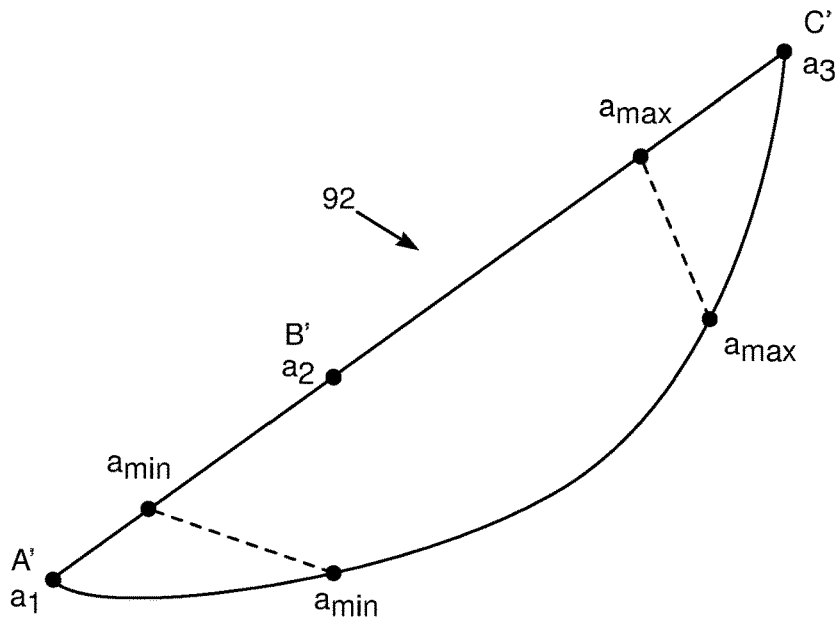
FIG. 4B is a schematic diagram illustrating a figure topologically equivalent to the triangle of FIG. 4A, according to an embodiment of the present invention.

FIG. 4A is a schematic diagram illustrating a typical triangle of mesh 82, and FIG. 4B is a schematic diagram illustrating a figure topologically equivalent to the triangle of FIG. 4A, according to an embodiment of the present invention. As illustrated in FIG. 4A, a triangle 90A of mesh 82 has vertices A, B, C, corresponding to positions 74. The vertices are joined by straight line segments AB, BC, CA, also herein referred to as edges AB, BC, CA, corresponding to line segments 78.

In the following description of the analysis of triangle 90A, vertices A, B, and C are assumed, as a general case, to have respective peak-peak voltages $a_1$, $a_2$, and $a_3$, typically measured in mV, where $a_1<a_2<a_3$. (Examples of degenerate cases, such as $a_1=a_2$, $a_2=a_3$, or $a_3=a_1$, are given below.)

A FIG. 92 is topologically equivalent to triangle 90A. FIG. 92 comprises a straight line segment A'B'C' and a curved line A'C', where A', B', C' respectively correspond to A, B, C. Segment A'B'C' may be considered to be a first number line, where A' has the value $a_1$, C' has the value $a_3$, and B' has the value $a_2$ (between $a_1$ and $a_3$). Curved line A'C' may be considered to be a second number line.

In embodiments of the present invention, tissue 15 is assumed to comprise scar tissue if the peak-peak voltages formed at the tissue, and acquired by electrodes 38, lie in a range between $a_{min}$ and $a_{max}$, where $a_{min}$ is a minimum peak-peak voltage value identifying scar tissue, and $a_{max}$ is a maximum peak-peak voltage value identifying the scar tissue. $a_{min}$ and $a_{max}$ are also typically measured in mV.

As is known in the art, scar tissue may be classified according to assigned values of $a_{min}$ and $a_{max}$. Table I gives some of these classifications, together with values of $a_{min}$ and $a_{max}$.

TABLE I

| Type of Scar Tissue | Approximate value of $a_{min}$ (mV) | Approximate value of $a_{max}$ (mV) |
|---|---|---|
| Dense | 0 | 0.5 |
| Hibernating Myocardium | 0.5 | 1.5 |

Processor 46 uses $a_{min}$ and $a_{max}$ in analyzing triangles 90. Typically $a_1<a_{min}$, $a_{max}<a_3$, and this inequality is assumed for triangle 90A. Examples of cases where the inequality, herein referred to as the boundary inequality, does not hold are provided below.

Prior to the analysis of the triangles, both values $a_{min}$, $a_{max}$ are typically pre-set by operator 15. In the analysis, processor 46 may position $a_{min}$, $a_{max}$ on curved number line A'C', and thus on edge AC at points D,E, as is illustrated in FIGS. 4A and 4B. In addition both values $a_{min}$, $a_{max}$ may be positioned on straight number line A'B'C'. By way of example, FIGS. 4A and 4B illustrate $a_{min}$ as being on line segment A'B', and thus on edge AB at a point F, and $a_{max}$ as being on line segment B'C', and thus on edge BC at a point G. However, it will be understood that both values $a_{min}$, $a_{max}$ may be positioned on line segment A'B', or both may be positioned on line segment B'C'.

From the description above it will be understood that edges AB, BC, and CA of triangle 90A are also considered herein as number lines, each of the lines terminating in two of the values $a_1$, $a_2$, and $a_3$. Points D, E, F, G are positioned on the number lines according the numerical values of the points, i.e., in accordance with $a_{min}$ and $a_{max}$.

Once values $a_{min}$, $a_{max}$ have been positioned on edges, i.e., number lines, of triangle 90A processor 46 constructs a first line DF joining the edge points $a_{min}$, and a second line EG joining the edge points $a_{max}$. A shaded region 94, of an area enclosed by polygon DFBGE comprises regions of the triangle that are assumed to have voltage values between $a_{min}$ and $a_{max}$, and thus to identify scar tissue.

FIG. 5 is a table illustrating numerical examples of different triangles 90, the polygons generated for the triangles, and the area of each of the polygons, according to an embodiment of the present invention. The table gives nominal cartesian coordinates (x,y) of the vertex of each triangle, and nominal peak-peak voltages ($a_1$, $a_2$, $a_3$) associated with each vertex. For each triangle there is an example of a nominal minimum and maximum peak-peak voltage ($a_{min}$, $a_{max}$). The diagram on the left of each row illustrates the triangle, with the generated polygon shown as a shaded region. The calculated area of each shaded region is also given, as well as the area of its triangle.

Triangles 1, 3, and 4 are examples of the degenerate cases referred to above. Triangles 1 and 2 are examples where the boundary inequality provided above does not hold.

Figure 6:
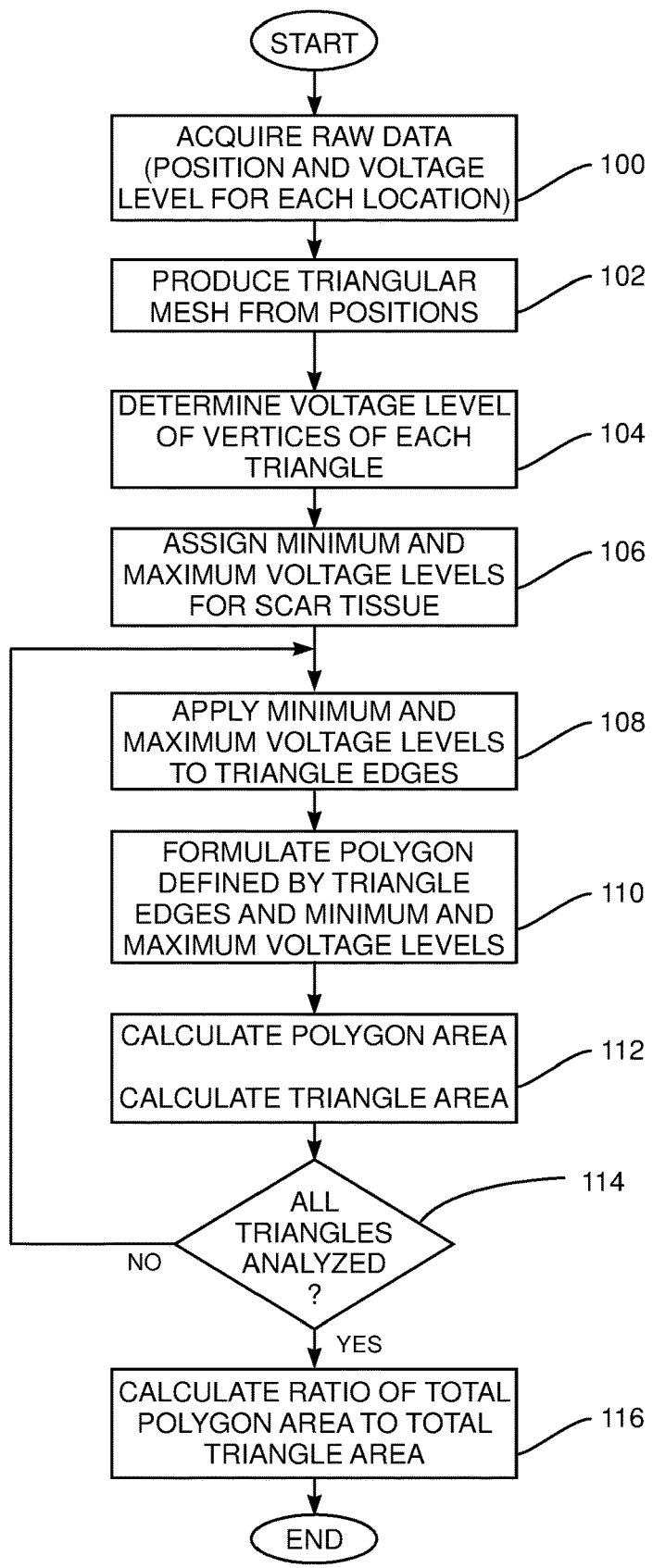
FIG. 6 is a flowchart of an algorithm implemented by a processor and/or a professional in analyzing tissue of a patient, according to an embodiment of the present invention.
Figure 7:
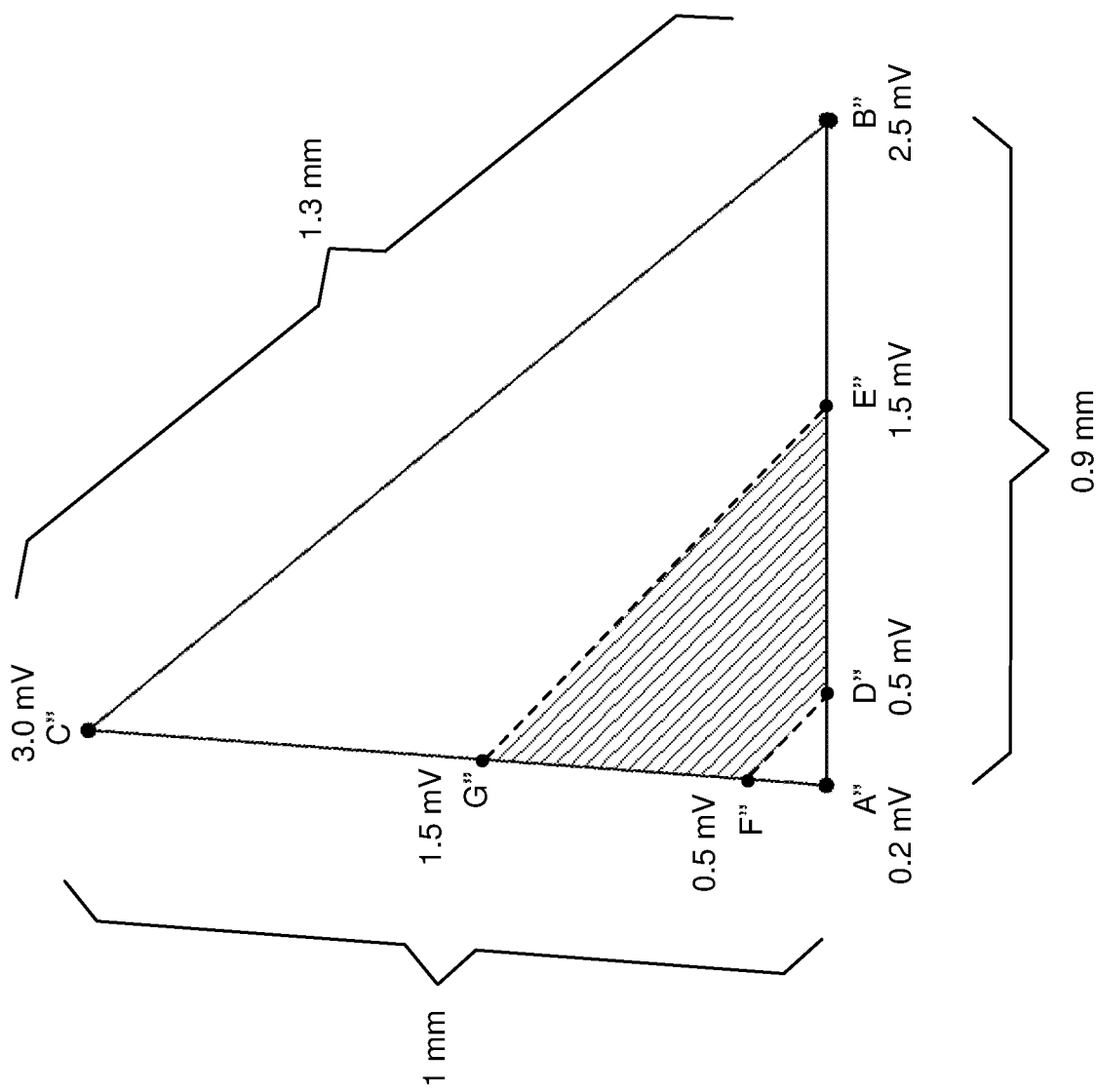
FIG. 7 is a schematic of a triangle illustrating steps of the algorithm, according to an embodiment of the present invention.

FIG. 6 is a flowchart of an algorithm implemented by processor 46 and/or professional 14 in analyzing tissue 15 of patient 18, and FIG. 7 is a schematic of a triangle illustrating steps of the algorithm, according to an embodiment of the present invention. In an initial step 100 of the algorithm, probe 26 is inserted into patient 18, electrodes 38 are used to acquire peak-peak voltages of locations of tissue 15, and the processor generates and records ordered pairs of positions and respective peak-peak voltages of the positions on the tissue, as described above.

In a mesh producing step 102, the processor produces a triangular mesh, comprising line segments joining the recorded positions found in step 100, and evaluates the lengths of the line segments of each of the triangles of the mesh.

For each triangle vertex, in a vertex voltage step 104, the processor assigns a peak-peak voltage to the vertex of each identified triangle.

In a scar bounding step 106, professional 14 selects values for minimum peak-peak voltage value $a_{min}$ and maximum peak-peak voltage value $a_{max}$ and provides the values to the processor.

For each given triangle of the mesh formed in step 102, in an analysis step 108 the processor analyzes each edge of the triangle and applies the values of $a_{min}$ and $a_{max}$ to the edges, as described above with respect to FIGS. 4A and 4B.

As is also described above with respect to FIGS. 4A and 4B, in a polygon formulation step 110, once the values of $a_{min}$ and $a_{max}$ have been applied to the edges of a given triangle, the processor delineates the polygon defined by the triangle edges and the applied values of $a_{min}$ and $a_{max}$.

The processor then calculates the area for the delineated polygon, and the area of the triangle containing the polygon, in an area calculation step 112.

FIG. 7 is an example of a triangle A"B"C" formed in step 102. By way of example, the lengths of the edges of triangle A"B"C" are assumed to be: A"B"=0.9 mm, B"C"=1.3mm, A"C"=1.0 mm.

In step 104, processor 46 assigns the vertices of the triangle, using the data acquired in step 100, the following peak-peak voltages: A" 0.2 mV; B" 2.5 mV; C" 3.0 mV.

In step 106 it is assumed that professional 14 selects values of $a_{min}$ and $a_{max}$ corresponding to hibernating myocardium, i.e., $a_{min}$=0.5 mV and $a_{max}$=1.5 mV.

In step 108 the processor applies the values of $a_{min}$ and $a_{max}$ to the edges of triangle A"B"C". This generates points D" with a value of 0.5 mV and E" with a value of 1.5 mV on edge A"B". The application also generates points F" with a value of 0.5 mV and G" with a value of 1.5 mV on edge A"C".

The processor may calculate the positions of points D", E", F", G" according to the lengths of the respective edges upon which they lie, and according to the values of the voltages of the vertices of the edges, considering the edges as number lines. Typical calculations are given in equations (1)-(4).

$$A''D'' = \frac{0.5 \text{ mV} - 0.2 \text{ mV}}{2.5 \text{ mV} - 0.2 \text{ mV}} \cdot 0.9 \text{ mm} = 0.117 \text{ mm} \quad (1)$$

$$A''E'' = \frac{1.5 \text{ mV} - 0.2 \text{ mV}}{2.5 \text{ mV} - 0.2 \text{ mV}} \cdot 0.9 \text{ mm} = 0.509 \text{ mm} \quad (2)$$

$$A''F'' = \frac{0.5 \text{ mV} - 0.2 \text{ mV}}{3.0 \text{ mV} - 0.2 \text{ mV}} \cdot 1.0 \text{ mm} = 0.107 \text{ mm} \quad (3)$$

$$A''G'' = \frac{1.5 \text{ mV} - 0.2 \text{ mV}}{3.0 \text{ mV} - 0.2 \text{ mV}} \cdot 1.0 \text{ mm} = 0.464 \text{ mm} \quad (4)$$

Using the positions of points D", E", F", G" the processor in step 110 delineates the polygon D"E"G"F".

In step 112 the processor calculates the area of polygon D"E"G"F" as 0.11145 mm². The processor also calculates the area of triangle A"B"C", for example from the lengths of the triangle sides or by any other suitable method for calculating the area of a triangle, giving the area as 0.449 mm².

Returning to the flowchart of the algorithm, the processor iterates steps 108, 110, and 112 for all triangles in the mesh generated in step 102, and in a comparison step 114 the processor checks if the iteration has been performed for all triangles. If comparison 114 returns negative, control of the flowchart returns to step 108. If comparison 114 returns positive, indicating that all triangles of the mesh have been analyzed, control continues to a final step 116 of the flowchart.

In final step 116 of the algorithm the processor sums the total area of all polygons identified for the mesh, and the total area of all the triangles of the mesh. The processor then calculates the ratio of the two areas, and provides the ratio to professional 14, typically using screen 62.

It will be understood that the ratio determined by the flowchart is a measure of the fraction of the total area of tissue 15 which lies between the scar identifying peak-peak minimum and maximum values $a_{min}$ and $a_{max}$. The ratio is also referred to herein as the scar burden associated with tissue 15. Professional 14 may use the ratio, i.e., the scar burden, to judge how scarred tissue 15 is, and also to decide if a procedure, such as ablation of a section of tissue 15, is to be performed.

The above description has described, by way of example, how a predefined range of bipolar voltages may be applied to vertices of triangles in a triangular mesh to evaluate a selected classification of scar burden, by calculating areas within the triangles of the mesh. Those having ordinary skill in the art will be able to adapt the description, mutatis mutandis, to evaluate the scar burden for other scar classifications. It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for assessing scarring of cardiac tissue, comprising:
   a probe comprising:
      one or more electrodes, which are configured to contact the cardiac tissue at a plurality of positions and to sense respective voltages in the tissue at the positions; and a processor which is configured to:
    receive the respective voltages,
    compute a triangular mesh that is representative of a surface of the cardiac tissue and comprises multiple triangles having vertices corresponding to the positions contacted by the one or more electrodes,
    calculate respective scar areas within the triangles by comparing the respective voltages sensed at the positions corresponding to the vertices to a predefined range of the voltages that is associated with scarring, wherein the range comprises a minimum voltage associated with the scarring of the tissue and a maximum voltage associated with the scarring of the tissue, and for a given triangle in the triangles, associating the minimum and maximum voltages with the edges of the given triangle so as to define points on the edges and joining the points to form a polygon, and wherein the polygon comprises, for the given triangle, the respective scar area, and
    compute a sum of the respective areas, and compare the sum to a total area of the triangles so as to assess a degree of the scarring of the tissue.

2. The apparatus according to claim 1, wherein the voltages comprise peak-peak bipolar voltages.

3. The apparatus according to claim 1, wherein the one or more electrodes comprise two electrodes.

4. The apparatus according to claim 1, wherein the probe further comprises a sensor configured to provide respective signals to the processor indicative of the positions.

5. The apparatus according to claim 1, wherein the one or more electrodes are configured to provide respective signals to the processor indicative of the positions.

6. The apparatus according to claim 1, wherein the predefined range is selected for the scarring of the tissue to comprise dense scar.

7. The apparatus according to claim 1, wherein the predefined range is selected for the scarring of the tissue to comprise hibernating myocardium.

8. A method for assessing scarring of cardiac tissue, comprising:
    contacting the cardiac tissue with one or more electrodes at a plurality of positions;
    sensing respective voltages in the tissue at the positions;
    computing a triangular mesh that is representative of a surface of the cardiac tissue and that comprises multiple triangles having vertices corresponding to the positions contacted by the one or more electrodes;
    calculating respective scar areas within the triangles by comparing the respective voltages sensed at the positions corresponding to the vertices to a predefined range of the voltages that is associated with scarring, wherein the range comprises a minimum voltage associated with the scarring of the tissue and a maximum voltage associated with the scarring of the tissue, and for a given triangle in the triangles, associating the minimum and maximum voltages with the edges of the given triangle so as to define points on the edges and joining the points to form a polygon, and wherein the polygon comprises, for the given triangle, the respective scar area; and
    computing a sum of the respective areas, and comparing the sum to a total area of the triangles so as to assess a degree of the scarring of the tissue.

9. The method according to claim 8, wherein the voltages comprise peak-peak bipolar voltages.

10. The method according to claim 8, wherein the one or more electrodes comprise two electrodes.

11. The method according to claim 8, and further comprising configuring a sensor to provide respective signals indicative of the positions.

12. The method according to claim 8, and further comprising configuring the one or more electrodes to provide respective signals indicative of the positions.

13. The method according to claim 8, and comprising selecting the predefined range so that the scarring of the tissue comprises dense scar.

14. The method according to claim 8, and comprising selecting the predefined range so that the scarring of the tissue comprises hibernating myocardium.

* * * * *